(12) United States Patent
Kabus et al.

(10) Patent No.: US 11,246,552 B2
(45) Date of Patent: Feb. 15, 2022

(54) ATTENUATION CORRECTION OF PET DATA OF MOVING OBJECT

(71) Applicant: KONINKLIJKE PHILIPS N.V., Eindhoven (NL)

(72) Inventors: Sven Kabus, Hamburg (DE); Andre Frank Salomon, Aachen (DE)

(73) Assignee: KONINKLIJKE PHILIPS N.V, Eindhoven (NL)

( * ) Notice: Subject to any disclaimer, the term of this patent is extended or adjusted under 35 U.S.C. 154(b) by 90 days.

(21) Appl. No.: 16/761,173

(22) PCT Filed: Nov. 7, 2018

(86) PCT No.: PCT/EP2018/080379
§ 371 (c)(1),
(2) Date: May 1, 2020

(87) PCT Pub. No.: WO2019/091989
PCT Pub. Date: May 16, 2019

(65) Prior Publication Data
US 2020/0337666 A1    Oct. 29, 2020

(30) Foreign Application Priority Data

Nov. 7, 2017  (EP) ..................................... 17200239

(51) Int. Cl.
*A61B 6/00*   (2006.01)
*G06T 11/00*  (2006.01)

(52) U.S. Cl.
CPC .......... *A61B 6/5235* (2013.01); *A61B 6/5258* (2013.01); *G06T 11/005* (2013.01)

(58) Field of Classification Search
None
See application file for complete search history.

(56) References Cited

U.S. PATENT DOCUMENTS

| 2008/0107229 A1* | 5/2008 | Thomas ................. A61B 6/469 378/4 |
| 2010/0046821 A1 | 2/2010 | Manjeshwar |
| 2012/0078089 A1 | 3/2012 | Wollenweber |

(Continued)

OTHER PUBLICATIONS

International Search Report for PCT/EP2018/080379 dated Feb. 20, 2019.

(Continued)

*Primary Examiner* — Hoon K Song (57) ABSTRACT

The invention relates to a system and a method for assisting in attenuation correction of gated PET data of a moving object (2). In the system, an evaluation unit (15) is configured to (i) receive a CT image of the object (2) and to segment the CT image into a plurality of CT sub-images, each CT sub-image correspond to an axial segment of an imaged volume, (ii) to determine for each CT sub-image a gate including PET data having a greatest correspondence with the CT sub-image, (iii) to construct, for each CT sub-image, a PET sub-image from the PET data included in the gate determined for the CT sub-image, the PET sub-image substantially corresponding to the same axial segment of the imaged volume as the CT sub-image, and (iv) to combine the PET sub-images to form a PET reference image of the object (2).

10 Claims, 3 Drawing Sheets

(56) References Cited

U.S. PATENT DOCUMENTS

| | | | | |
|---|---|---|---|---|
| 2013/0281825 | A1* | 10/2013 | Thiruvenkadam ... | A61B 6/5247 600/411 |
| 2014/0056500 | A1* | 2/2014 | Bal ..................... | G06T 11/005 382/131 |
| 2015/0221104 | A1 | 8/2015 | Ra | |
| 2016/0163042 | A1* | 6/2016 | Wollenweber ........ | G06T 11/003 382/131 |
| 2016/0174919 | A1* | 6/2016 | Ahn .................... | A61B 5/0059 382/131 |

OTHER PUBLICATIONS

Dawood, Mohammad et al "Motion Correction in Respiratory Gated Cardiac PET/CT Using Multi-Scale Optical Flow", Network and Parallel Computing; MICCAI 2008, Part II, LNCS 5242, pp. 155-162.

Lamare, F. et al "List-Mode-Based Reconstruction for Respiratory Motion Correction in PET using Non-Rigid Body Transformations", Physics in Medicine and Biology, vol. 52, No. 17, Sep. 2007, pp. 5187-5204.

* cited by examiner

ATTENUATION CORRECTION OF PET DATA OF MOVING OBJECT

FIELD OF THE INVENTION

The present invention is related to motion-compensated positron emission tomography (PET) imaging. More specifically, the invention relates to a system and a method for assisting in attenuation correction of PET data of a moving object from PET data associated with a plurality of gates, each gate being associated with one of plurality of motion phases of the motion and including PET data acquired during the respective motion phase.

BACKGROUND OF THE INVENTION

In nuclear medicine, PET imaging is particularly performed to visualize and quantitatively assess the metabolism state of a patient. For instance, a PET image can help to localize pathologic processes, such as tumor-growth or inflammation, and areas of abnormal blood perfusion in organs.

In PET, a positron-emitting substance is administered to the patient. The substance, which is usually also referred to as radio pharmaceutical or radiotracer, is selected such that it is adsorbed by cells which are involved in the pathological processes to be examined. When a positron is emitted by the radiotracer, an encounter with a nearby electron annihilates the electron positron pair and produces a pair of annihilation photons. Each of these annihilation photons has an energy of 511 keV and both photons travel in substantially opposite directions. These photons are recorded by the PET detector substantially at the same time as a so-called coincidence. From such coincidences, PET systems reconstruct an activity distribution or activity map, which shows the spatial distribution of the electron positron annihilation rate within the patient and which is also referred to as PET image herein. The activity distribution or PET image substantially corresponds to the spatial distribution of the radiotracer within the object, which can thus be evaluated for diagnostic purposes.

Usually, the activity distribution is determined on the basis of true coincidences, i.e. coincidences comprising two annihilation photons that travel unimpeded to the PET detector and hit the detector at opposing locations with their original energy of 511 keV. However, not all annihilation photons reach the detector unimpeded due to photon attenuation. Attenuation particularly occurs when a photon is absorbed before it reaches the detector or when it undergoes inelastic Compton scattering one or more times (where a scattered photon may reach the detector but has a lower energy).

In order to take account of these effects, attenuation correction is performed when determining the activity map. Without such attenuation correction, regions having a high activity and a high attenuation probability for photons originating from this region would appear as regions with a smaller activity.

Attenuation correction requires the knowledge of a so-called attenuation map or attenuation distribution, which provides the spatial distribution of the photon attenuation rate. In order to determine the attenuation map, computed tomography (CT) imaging may be performed in addition to the PET imaging. CT images correspond to attenuation maps for X-ray photons and can be up-scaled to the energy of the annihilation photons to determine the attenuation map. Accordingly, mixed modality scanners comprising a PET scanner and a CT imaging device have become popular in the clinical field.

Further, respiratory motion during the acquisition of PET images can cause significant errors in a PET image-based assessment of metabolic parameters and the precise localization of pathological processes. Therefore, several attempts have been made to compensate for respiratory motion in PET images. Respiratory motion compensation is usually performed on the basis of gated PET imaging. Here, the acquired PET data are separated into so-called gates or bins, where each gate contains the PET data acquired during one phase of the respiratory motion. In order to further evaluate the PET images, one PET image from a particular gate may be selected and the other PET images may be mapped onto this PET image by means of image registration.

One problem occurring in connection with gated PET imaging relates to attenuation correction. A CT scan for determining the attenuation map usually takes some seconds and during such a scan, the CT scanner is moved relative to the patient in the axial direction (z-direction) to image several slices. In so doing, narrower slices of the patient can be imaged without respiratory motion blurring. However, the motion state of the patient usually varies for different slices so that the CT image reconstructed from the scan shows the patient anatomy in different motion phases. As a result, the motion phase varies along the z-direction of the CT image. So, as an example, the superior part of the CT image may be acquired in the inhale state while the inferior part of the CT image may be acquired in the exhale state. Thus, for each PET gate, there is a mismatch between at least part of the CT image and the PET data, which leads to an inaccurate PET attenuation correction when the attenuation map for the binned PET data is determined using the CT image.

In some cases, the CT image could be acquired in breath-hold of the patient to avoid this problem. However, this results in discomfort for the patient and for certain patients a breath hold is not possible at all.

SUMMARY OF THE INVENTION

It is therefore an object of the present invention to allow for an accurate attenuation correction of PET images of a moving object, particularly a patient body undergoing respiratory motion.

In accordance with one aspect, the invention suggests a system for assisting in attenuation correction of PET data of a moving object motion, the PET data being associated with a plurality of gates, each gate being associated with one of plurality of motion phases of the motion of the object and including PET data acquired during the respective motion phase. The system comprises an evaluation unit which is configured to receive a CT image of the object and to segment the CT image in an axial direction of the object into a plurality of CT sub-images, each CT sub-image corresponding to an axial segment of an imaged volume, determine, for each CT sub-image, a gate including PET data having a greatest correspondence with the CT sub-image in accordance with a predetermined criterion, construct, for each CT sub-image, a PET sub-image from the PET data included in the gate determined for the respective CT sub-image, the PET sub-image substantially corresponding to the same axial segment of the imaged volume as the respective CT sub-image, and combine the PET sub-images to form a PET reference image of the object.

The system is further configured to provide the PET reference image for attenuation correction of the PET data on the basis of the CT image.

Since the PET reference image is slice-wise assembled from PET sub-images which are aligned with the CT sub-images in terms of the motion phases of the motion of the object, the PET reference image is substantially aligned with the CT image for all axial positions. Therefore, the alignment of the PET data with the PET reference image allows for an easy and accurate attenuation correction of the PET data using the CT image.

For instance, the attenuation correction of a PET image can easily be performed on the basis of the CT image upon having registered the PET image with the PET reference image. In particular, this is less complex and less error-prone compared to a registration between the binned PET data and CT image.

In one embodiment of the invention, the evaluation unit is configured to determine for each gate a transformation for registering the PET data included in the respective gate with a CT sub-image and to determine the gate including the PET data having the greatest correspondence with said CT sub-image on the basis of a comparison between the transformations pertaining to the PET gates. In this manner, the PET data having the greatest correspondence with the CT sub-image can be determined efficiently and reliably.

In a related embodiment, the transformations are rigid transformations and/or affine transformations. Such transformations can be determined with less computational effort compared to the determination of other transformation, such as, for example, elastic transformations. However, the invention is not limited to rigid or affine transformation. Rather, elastic transformations may likewise be determined in order to find the PET data having the greatest correspondence with the CT sub-images. Such transformations may allow for a greater accuracy and robustness of the determination.

In a further related embodiment, the predetermined criterion is selected such that PET data in a gate for which a transformation with a smaller displacement in the axial direction of the object has been determined have a greater correspondence with the CT sub-image than PET data in a gate for which a transformation with a larger displacement in the axial direction of the object has been determined. Since the motion state of the object as shown in the CT image varies in the axial direction as explained above, this criterion allows for an accurate determination of the PET gates including PET data having the greatest correspondence with the CT sub-images.

In order to determine the PET gates including PET data having the greatest correspondence with the CT sub-images in accordance with this criterion, the evaluation unit may be configured to extract a displacement in the axial direction from each transformation and to determine the gate including PET data having the greatest correspondence with the CT sub-image on the basis of the extracted displacements.

However, the displacements in other directions may likewise be taken into consideration in order to increase accuracy. Therefore, a further embodiment of the invention includes that the evaluation unit is configured to extract a displacement in at least one further direction from each transformation and to additionally determine the gate including PET data having the greatest correspondence with the CT sub-image on the basis of the extracted displacements in the at least one further direction. The further direction may particularly be perpendicular to the axial direction. In case the object comprises a section of a patient body, the further direction may particularly correspond to the anterior-posterior direction and/or the left-right direction.

In one embodiment, the object comprises a section of a patient body undergoing respiratory motion and the evaluation unit is configured to further determine the gate including PET data having the greatest correspondence with the CT sub-image on the basis of a respiration model, the respiration model specifying an expected course of displacements occurring in the object during its motion in time. In particular, the respiration model may specify an expected course of displacements in the axial direction occurring in the object during its motion in time. The respiration model may particularly be used in case similar displacements have been determined for the PET data of several PET gates such that all these PET data have a similar correspondence with a CT sub-image and/or if unexpected displacements have been determined. Particularly in these cases, the PET data having the greatest correspondence with a CT sub-image may additional be selected on the basis of the respiration model. Hereby, the robustness of construction of the PET reference image can be increased.

In a further embodiment, the moving object undergoes an essentially cyclic motion. In this case, the amount of PET data acquired in each motion phase is higher than in case of a non-cyclic motion (since each motion phase occurs several times during the PET scan), so that the PET reference image can be constructed more accurately and reliable. However, the invention is not restricted to the imaging of objects undergoing cyclic motions and may likewise be applied with respect to moving objects undergoing non-cyclic motions.

In accordance with a further aspect, the invention suggests a method for assisting in attenuation correction of PET data of a moving object, the PET data being associated with a plurality of gates, each gate being associated with one of plurality of motion phases of the motion of the object and including PET data acquired during the respective motion phase, the method comprises the following steps:

receiving a CT image of the object and segmenting the CT image in an axial direction of the object into a plurality of CT sub-images, each CT sub-image corresponds to an axial segment of an imaged volume, determining, for each CT sub-image, a gate including PET data having a greatest correspondence with the CT sub-image in accordance with a predetermined criterion, constructing, for each CT sub-image, a PET sub-image from the PET data included in the gate determined for the respective CT sub-image, the PET sub-image substantially corresponding to the same axial segment of the imaged volume as the respective CT sub-image, and combining the PET sub-images to form a PET reference image of the object, and providing the PET reference for attenuation correction of the PET data on the basis of the CT image.

In accordance with a further aspect, the invention suggests a computer program comprising program code for causing a computer device to carry out the method, when the computer program is executed in the computer device.

It shall be understood that the system of claim 1, the method of claim 9 and the computer program of claim 10 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings:

FIG. 1 schematically and exemplarily illustrates components of a an imaging system comprising a PET scanner and a CT scanner, FIG. 2 schematically and exemplarily illustrates a result of an evaluation of axial displacements included in transformations for registering binned PET data with CT sub-images, and FIG. 3 schematically and exemplarily illustrates steps of a procedure for generating a PET reference image for use in attenuation correction of the PET data.

DETAILED DESCRIPTION OF EMBODIMENTS

Figure 1:
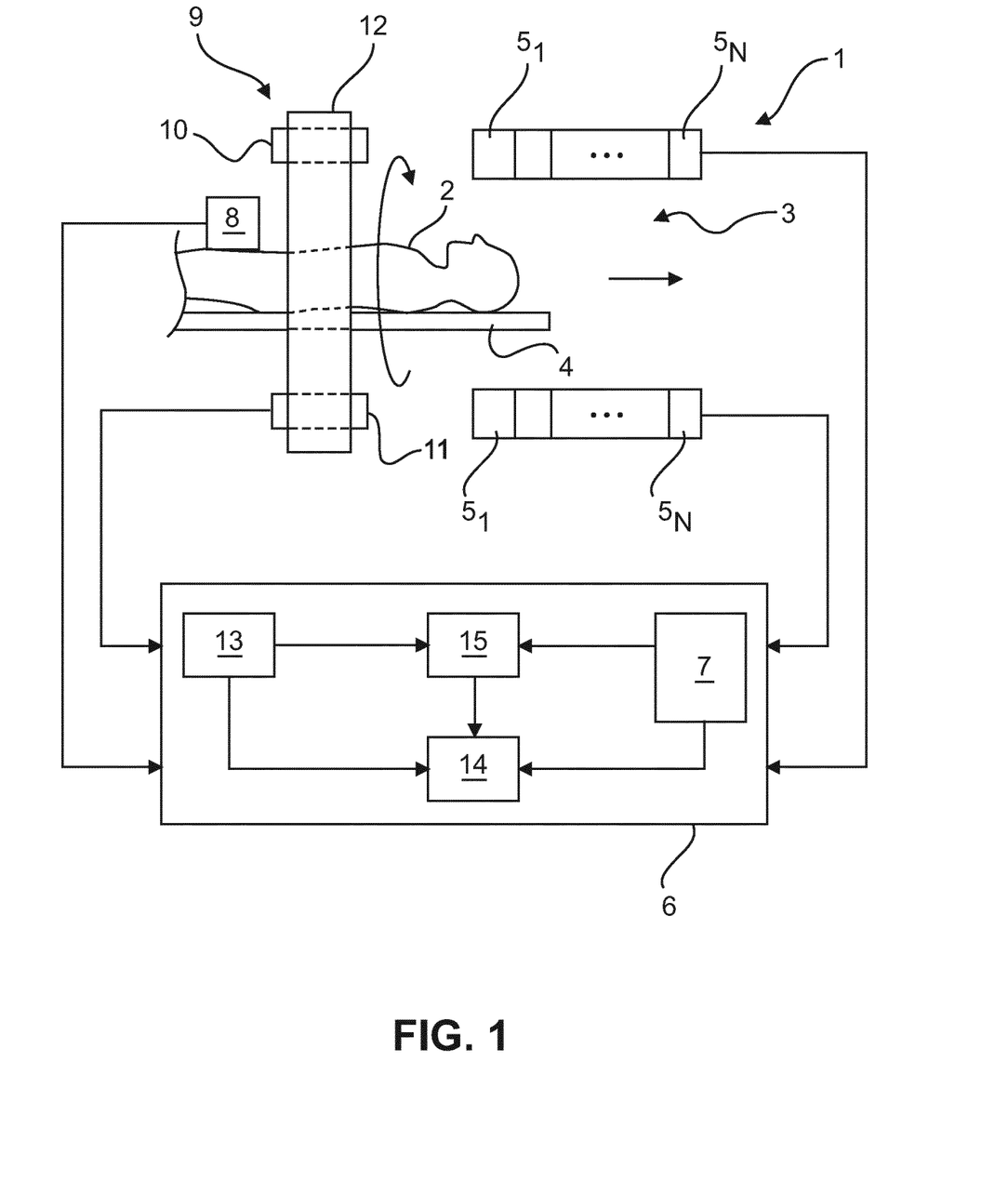

FIG. 1 schematically and exemplarily shows components of an imaging system for imaging an object 2. The imaging system may be used in a clinical application and the object 2 may be a human or animal patient body or a part thereof. The imaging system comprises a PET scanner 1 for acquiring PET images of the object 2. In addition, the imaging system comprises a CT scanner 9 for acquiring three-dimensional CT images of the object. As will be explained in more detail herein below, the CT images are particularly used for carrying out an attenuation correction of the PET images taking into consideration respiratory motion of the patient body, which may be substantially cyclic.

The PET scanner 1 may include a substantially cylindrical PET scanner volume 3 accommodating the patient body 2 during operation of the imaging system. The longitudinal axis of the PET scanner volume 3 is also referred to as z-axis herein and defines an axial direction, which is also referred to as z-direction herein. The patient body 2 may be supported by a patient table 4 that is movable into and out of the PET scanner volume 3 in the axial direction by means of a controllable drive unit (not shown in the figures). During a PET scan, the patient may be arranged in the PET scanner volume in such a way that the longitudinal axis of the patient body 2 is aligned with the longitudinal axis of the PET scanner volume 3 (i.e. the z-axis).

The PET scanner volume 3 corresponds to the inner volume defined by a substantially cylindrical detector assembly (which is shown in FIG. 1 in a longitudinal section). The detector assembly may be made up of multiple detector rings $5_1, \ldots, 5_N$ that are arranged adjacent to each other along the central longitudinal axis of the cylindrical PET scanner volume 3. Each detector ring $5_i$ may include multiple detector elements, where each detector element covers a certain (small) angle range of the corresponding detector ring $5_i$ and allows for detecting photons entering the detector element from the PET scanner volume 3 and for measuring their energy.

The PET scanner volume 3 may have a length of about 10-50 cm in the axial direction so that a section of the patient body 2 having a corresponding axial length can be imaged by means of the PET scanner 1 in one scan (however, it may likewise also be possible to image the whole patient body in one scan using a suitable gantry). The duration of such a scan may be between some minutes and some ten minutes. If multiple sections of the patient body 2 are to be imaged, this may done in several scans and the procedure for determining a reference image as described herein may be applied for each scan.

By means of the PET scanner 1 and the detector rings $5_1, \ldots, 5_N$ included therein, PET raw data are acquired in a way known to a person skilled in the art as such during a PET scan of the object 2. In particular, a radiotracer may be administered to the patient, which accumulates at the structures of interest within patient body 2 and which emits positrons. When the positrons encounter nearby electrons, the electron positron pairs annihilate and produce pairs of annihilation photons, which are recorded by means of the PET scanner 1. In particular, the PET scanner 1 may detect true coincidences, i.e. annihilation photons with energies of 511 keV traveling in opposite directions, and may register the positions within the detector rings $5_1, \ldots, 5_N$ (i.e. the detector elements) where the annihilation photons enter the detector rings $5_1, \ldots, 5_N$ (i.e. the detector elements).

The PET raw data are forwarded to a processing unit 6 for further processing. The processing unit 6 particularly comprises a PET reconstruction unit 7 which is configured to reconstruct PET data from the raw data, which are also referred to as PET images. The PET data or PET images particularly correspond to an activity map indicating the spatial distribution of the electron positron annihilations in the patent, as detected by the PET scanner 1 (i.e. without corrections, such as attenuation correction and motion correction).

Given the scan time of some minutes to some ten minutes, a PET scan comprises a plurality of cycles of a respiratory motion of the patient body. In view of this, a motion correction may be carried out in order to avoid blurring of the PET images. To this end, the cycle of the respiratory motion is divided into two or more predetermined motion phases. Further, the PET data are separated into gates or bins in accordance with the motion phases during which the PET data (or the underlying raw data) are acquired. For this purpose, the respiratory motion may be monitored by means of a gating unit 8. The gating unit 8 may be configured to provide a gating signal which indicates the current motion phase or which notifies about transitions between motion phases. Based on this gating signal, the PET data may be assigned to the provided gates.

The gating unit 8 may be configured in any way known to a person skilled in art. In one possible implementation, the gating unit 8 includes a flexible belt which is placed around the patient body in such a way that it is expanded and contracted with respiration. The expansion and contraction motion is measured using a suitable measuring technique, such as, for example, a resistance-based or an inductance based technique, order to generate the gating signal.

Further, the imaging system comprises a CT scanner 9 for acquiring CT image data. The CT scanner 9 comprises an x-ray source 10 and an x-ray detector 11, which are mounted opposite to each other on a gantry 12, which is rotatable around an examination region of the CT scanner 9. The CT scanner 9 may be arranged adjacent to the PET scanner 1 in the axial direction of the PET scanner volume 3 such that the patient table 4 and the patient body 2 arranged thereon move through the examination region of the CT scanner 9 when the patient table 4 is moved along the axial direction into the PET scanner volume 3.

A CT scan may be performed during the movement of the patient table 4 into the PET scanner volume 3, and during a CT scan, the x-ray detector 11 and the x-ray source 10 are rotated around the patient body 2. In so doing, slices of the patient body may be consecutively imaged in such a way that the x-ray detector 11 is rotated around the patient 2 within a pre-defined angular range at adjacent positions along the z-direction. Alternatively, the x-ray detector 11 may be moved along a helical trajectory around the patient 2 during the scan.

The data acquired by means of the x-ray detector 11 during a scan may also be transmitted to the processing unit 6 and may be further processed in a CT reconstruction unit 13. The CT reconstruction unit 13 may reconstruct CT images on the basis of the acquired data using a reconstruction procedure known to the skilled in the art.

In the present imaging system, a CT image of the patient is particularly acquired in order to determine an attenuation map for performing an attenuation correction of the PET data in an attenuation correction unit 14 of the processing system. For this purpose, a CT scan of the patient body 2 may be performed using the CT scanner 1 prior to the PET scan. In one embodiment, the CT scan may be a helical low-dose scan carried out with a low x-ray radiation dose. Given a typical axial velocity of the x-ray detector 11 in this imaging mode, which may be 5 cm/s, for example, such a scan may be performed in some seconds.

Thus, the CT scan usually only comprises one or very few cycles of the respiratory motion of the patient body. As a consequence, the motion phase varies along the axial direction of the CT image. As a consequence, there is mismatch for each of the gates between the PET image pertaining to the gate and the CT image. Thus, a direct attenuation correction of the PET image on the basis of the CT image would lead to inaccuracies so that a precise quantification of the location and shape of relevant structures, such as tumors, would not be possible.

In order to allow for a more accurate attenuation correction of the PET data, it is suggested to construct a PET reference image, which is slice-wise assembled from the binned PET data in such a way that it shows the same motion state of the respiratory motion as the CT image substantially for all axial positions. In order to carry out the attenuation correction of a PET image using the CT image, the attenuation correction unit 14 may align the respective PET image with the PET reference image by means of an image registration procedure using a transformation. By construction, the PET image aligned with the PET reference image is also in alignment with the CT image. Thus, the attenuation correction of the aligned PET image can be carried out in a conventional manner on the basis of the CT image.

The PET reference image may be constructed in an evaluation unit 15 of the processing unit 6. In the following, embodiments of the procedure for generating the PET reference image will be explained. In these embodiments, the procedure may be carried out using the binned PET images as reconstructed in the PET reconstruction unit 7.

Optionally, the binned PET images may also be filtered by applying a median filter to each PET image. Hereby, image noise is reduced and, thus, a more robust construction of the PET reference image can be achieved. Moreover, the procedure is carried out on the basis of the CT image and it is assumed that the imaged volume of the CT image corresponds to the imaged volume of the PET images (if the imaged volume of the actual CT image is larger, it may be cropped accordingly).

In a further variant, the PET reference image may not be constructed on the basis of PET images which are separately generated for each PET gate. Rather, adjacent PET gates may be combined and the PET images provided for constructing the reference image may be generated from the PET data included in the combined PET gates. Hereby, the signal-to-noise ratio of the PET images can be improved. Therefore, this variant may be applied if the PET images generated on the basis of the original PET gates do not provide a sufficiently high signal-to-noise-ratio. In the following, this variant will not be further addressed explicitly. However, it is to be understood that the terms "gate" and "bin" either denote an original PET gate or a combined PET gate in the following.

In order to construct the reference, the evaluation unit 15 receives the CT image (step 301 in FIG. 3) and may define N axial segments of the image volume of the CT image and the PET images, where each axial segment includes an image volume corresponding to a certain interval of the z-axis. In other words, each axial segment comprises all image voxels at positions having z-coordinates within a certain interval. The axial segments are preferably defined such that entire imaged volume is covered by the axial segments. In one implementation, the axial segments may be defined by dividing the z-axis of the field of view into N disjoint intervals. However, the intervals do not necessarily have to be disjoint. Rather, it is also possible to define N overlapping intervals.

In the next step (step 302 in FIG. 3), the evaluation unit 15 constructs one CT sub-image from the CT image for each of the N axial segments, where the sub-image for each slice comprises the portion of the CT image corresponding to the slice. Thus, the i-th sub-image is generated by cutting all voxels outside the i-th section from the CT image. As a result of this step, the CT image is segmented along the axial direction of the patient body 2 into N CT sub-images.

As said above, the motion phase of the respiratory motion of the patient body 2 usually varies along the axial direction of the CT images. The N sections are preferably selected such that each of the CT sub-images shows a section of the patient in essentially the same motion state. In particular, the sections may be defined such that each CT sub-image shows the relevant section of the patient body in the same motion phase of the motion phases underlying the gating of the PET data.

Figure 3:
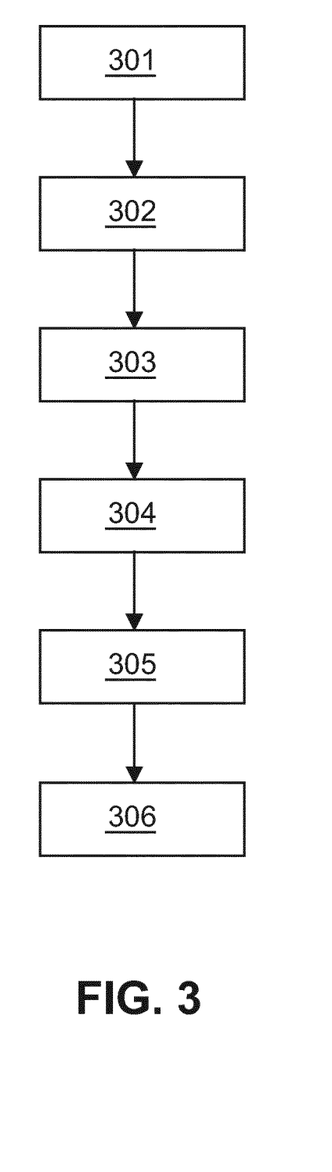

For each of the N sections, the evaluation unit 15 then compares the related CT sub-image with the binned PET images and determines the PET image having the greatest correspondence with the CT sub-image in accordance with a predetermined correspondence criterion (step 303 in FIG. 3). For this purpose, the evaluation unit 15 may determine for each of the PET images a transformation for registering the CT sub-image with the PET image. The transformation may be determined on the basis of a PET image which is spatially aligned with the CT sub-image in accordance with the nominal positions of the field-of-view of the PET image and the field-of-view of the CT sub-image. Then, the evaluation unit 15 may compare the determined transformations on the basis of a predetermined criterion in order to determine the PET image having the greatest correspondence with the CT sub-image.

In one embodiment, the transformations are rigid transformations. This means that they only contain rotations and displacements (translations). In order to compare the transformations, the evaluation unit 15 may extract the displacement in the axial direction included in each of the transformations. Then, the evaluation unit 15 may determine the transformation with the smallest displacement into the axial direction in terms of absolute values. Ideally, this smallest displacement substantially equals zero. Upon having determined the smallest displacement, the evaluation unit 15 identifies the PET image for which the transformation including the determined displacement has been calculated to register the CT sub-image with the PET image. This PET image has the greatest correspondence with the CT sub-image.

Figure 2:
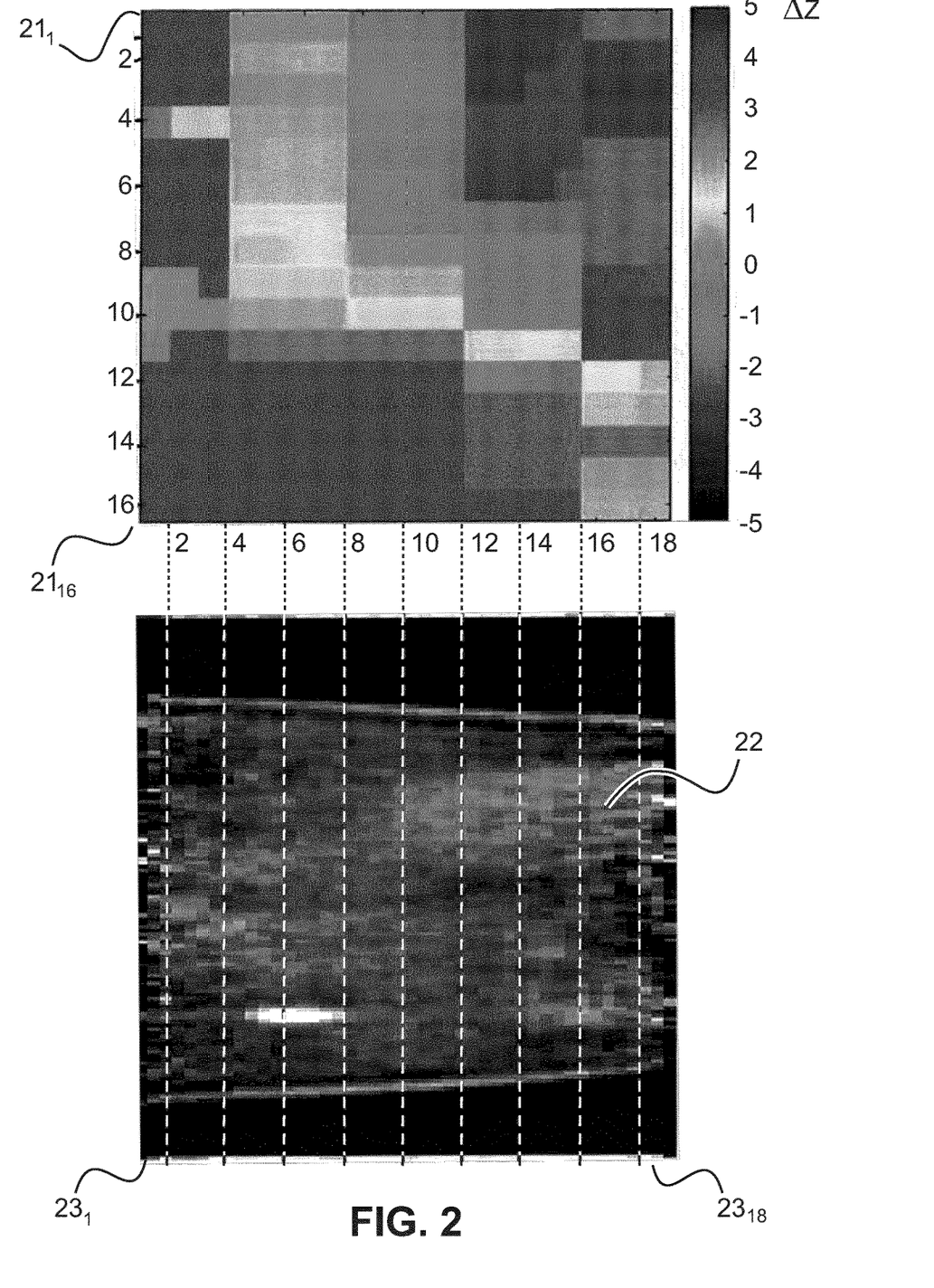

FIG. 2 schematically illustrates a result of an evaluation of axial displacements included in transformations for registering binned PET data with CT sub-images in one exemplary situation. In this situation, the PET data are subdivided into 16 gates $21_1, \ldots, 21_{16}$ and the z-axis of the imaged volume 22 is subdivided into 18 segments $23_1, \ldots, 23_{18}$. In the diagram in the upper part of FIG. 2, the values of the displacements Δz in z-direction (i.e. the axial direction) are illustrated, which are included in the transformation for registering the CT sub-images with the binned PET data. These displacements Δz are indicated by means of grey levels in the diagram.

In an optional variant of the aforementioned embodiment, the evaluation unit 15 may additionally select the PET image having the greatest correspondence with the CT sub-image on the basis of a respiration model, which describes the course of the axial displacements occurring in the patient body 2 during the breathing cycle in time. Hereby, the robustness of the construction of the PET reference image can be increased.

The respiration model may particularly be used in case similar displacements in z-direction, i.e. displacements within a predetermined interval, have been determined for several PET images such that all these PET images are possible selection candidates. In this case, the evaluation unit 15 may select the PET image from a gate, which is expected to provide the PET image having the greatest correspondence with the CT sub-image in accordance with the respiration model. For instance, if the displacements determined for PET images of consecutive PET gates are 2 mm, 1 mm, −1 mm and −1 mm, the evaluation unit 15 may select the PET image of the third gate because this PET image is expected to most likely belong to the same motion state as the respective CT sub-image in accordance with the respiration model.

In a further variant, the evaluation unit 15 may validate the series of selected PET gates on the basis of a respiration model and may change the selection on the basis of the result of this validation. When consecutive CT sub-images pertain to consecutive phases of the breathing motion, the series of selected PET gates should correspond to the same consecutive phases of the breathing motion. Therefore, the validation may include if this is the case or if order of the selected PET gates does not correspond to the course of the breathing motion. In the latter case, the evaluation unit 15 may change a selected PET gate which does not fit into this order and replace it with a better fitting PET gate. For instance, if the series of selected PET gates includes the gates 6, 7, 10 and 9 (in this order), the validation on the basis of the respiration model may result in the finding that the selection of the gate 10 was not optimal and the evaluation unit 15 may select gate 8 instead.

Upon having determined for each CT sub-image and the related axial segments an associated PET image, which has the greatest correspondence with the respective CT sub-image in a way described above, the evaluation unit 15 may construct the PET reference image on the basis of the determined PET images. For this purpose, the evaluation unit 15 may crop each of the PET images in such a way that it corresponds to the associated axial segment in order to generate a related PET sub-image (step 304 in FIG. 3). Then, the evaluation unit 15 may generate the PET reference image by assembling the PET sub-images (step 305 in FIG. 3). This may be done by stitching the PET sub-images together. The assembling is made in accordance with the order of the axial segments in the imaged volume. Thereupon, the constructed reference image may be provided to the attenuation correction unit 14 (step 306 in FIG. 3) so that this unit can perform an attenuation correction on the basis of the CT image using the reference image.

In the exemplary embodiment described above, the PET images or gates used for assembling the PET reference image have been selected on the basis of the axial displacements included in a rigid transformation for registering the PET images with the CT sub-images. In a further embodiment, the displacement in the y-direction (i.e. the posterior-anterior direction with respect to the patient body) and optionally also the displacement in the x-direction (i.e. the left-right direction of the patient body) included in each transformation may likewise be taken into consideration when selecting the PET images for assembling the PET reference image. Hereby, the movement of the patient body in anterior-posterior direction and optionally also in left-right direction can additionally be taken into account in order to achieve a more accurate result.

Thus, in this embodiment, the evaluation unit 15 may determine the PET image having the greatest correspondence with a CT sub-image on the basis of the displacements in z-direction and in y-direction and optionally also in x-direction, which are included in the (rigid) transformation for registering the PET image with the CT sub-image. In particular, the evaluation unit 15 may calculate for each PET image the quantity $(\Delta y)^2 + (\Delta z)^2$ or $(\Delta x)^2 + (\Delta y)^2 + (\Delta z)^2$, where Δx, Δy and Δz are the displacements in x-, y-direction and z-direction included in the transformation for registering the respective PET image with the CT sub-image, and may select the PET image associated with the smallest value of this quantity.

In a further embodiment, the PET images may be registered with the CT sub-images using an affine transformation, which includes scaling in addition to rotation and translation. In this case, the PET image having the greatest correspondence with A CT sub-image may additionally be determined on the basis of the amount of scaling, where a smaller amount of scaling may result in a greater correspondence.

Moreover, the transformation may be configured as an elastic transformation, which may be described by a deformation vector field including a deformation vector for each image voxel indicating the transformation of this voxel. In this case, the PET image having the greatest correspondence with the CT sub-image may likewise be selected on the basis of the mean displacement of all voxels in the z-direction and optionally in the x-direction and/or y-direction as explained above. However, the individual displacements of the voxels may be used to determine a robustness indicator which may additionally be taken into consideration during the selection of the PET image.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for assisting in attenuation correction of PET data of a moving object (2), the PET data being associated with a plurality of gates ($21_i$), each gate ($21_i$) being associated with one of plurality of motion phases of the motion of the object (2) and including PET data acquired during the respective motion phase, the system comprising an evaluation unit (15) configured to receive a CT image of the object (2) and to segment the CT image in an axial direction of the object (2) into a plurality of CT sub-images, each CT sub-image corresponding to an axial segment ($23_i$) of an imaged volume (22), determine, for each CT sub-image, a gate ($21_i$) including PET data having a greatest correspondence with the CT sub-image in accordance with a predetermined criterion, construct, for each CT sub-image, a PET sub-image from the PET data included in the gate ($21_i$) determined for the respective CT sub-image, the PET sub-image substantially corresponding to the same axial segment of the imaged volume (22) as the respective CT sub-image, and combine the PET sub-images to form a PET reference image of the object, and the system further being configured to provide the reference image for attenuation correction of the PET data on the basis of the CT image.

2. The system as defined in claim 1, wherein the evaluation unit (15) is configured to determine for each gate ($21_i$) a transformation for registering the PET data included in the respective gate with a CT sub-image and to determine the gate including the PET data having the greatest correspondence with said CT sub-image on the basis of a comparison between the transformations pertaining to the PET gates.

3. The system as define in claim 2, wherein the transformations are rigid transformations or affine transformations.

4. The system as defined in claim 2, wherein the predetermined criterion is selected such that PET data in a gate ($21_i$) for which a transformation with a smaller displacement in the axial direction of the object (2) has been determined have a greater correspondence with the CT sub-image than PET data in a gate ($21_i$) for which a transformation with a larger displacement in the axial direction of the object (2) has been determined.

5. The system as defined in claim 2, wherein the evaluation unit (15) is configured to extract a displacement in the axial direction from each transformation and to determine the gate ($21_i$) including PET data having the greatest correspondence with the CT sub-image on the basis of the extracted displacements.

6. The system as defined in claim 5, wherein the evaluation unit (15) is configured to extract a displacement in at least one further direction from each transformation and to additionally determine the gate ($21_i$) including PET data having the greatest correspondence with the CT sub-image on the basis of the extracted displacements in the at least one further direction.

7. The system as defined in claim 5, wherein the object (2) comprises a section of a patient body undergoing respiratory motion and wherein the evaluation unit (15) is configured to further determine the gate including PET data having the greatest correspondence with the CT sub-image on the basis of a respiration model, the respiration model specifying an expected course of displacements occurring in the object (2) during its motion in time.

8. The system as defined in claim 1, wherein the moving object (2) undergoes an essentially cyclic motion.

9. A method for assisting in attenuation correction of PET data of a moving object, the PET data being associated with a plurality of gates ($21_i$), each gate ($21_i$) being associated with one of plurality of motion phases of the motion of the object (2) and including PET data acquired during the respective motion phase, the method comprising:

receiving (301) a CT image of the object (2) and segmenting (302) the CT image in an axial direction of the object into a plurality of CT sub-images, each CT sub-images correspond to an axial segment ($23_i$) of an imaged volume (22), determining (303), for each CT sub-image, a gate ($21_i$) including PET data having a greatest correspondence with the CT sub-image in accordance with a predetermined criterion, constructing (304), for each CT sub-image, a PET sub-image from the PET data included in the gate ($21_i$) determined for the respective CT sub-image, the PET sub-image substantially corresponding to the same axial segment of the imaged volume as the respective CT sub-image, and combining (305) the PET sub-images to form a PET reference image of the object (2), and providing (306) the PET reference for attenuation correction of the PET data on the basis of the CT image.

10. A computer program comprising program code for causing a computer device to carry out a method as defined in claim 9, when the computer program is executed in the computer device (6).

* * * * *